(12) United States Patent
Patel et al.

(10) Patent No.: US 6,210,359 B1
(45) Date of Patent: Apr. 3, 2001

(54) NEEDLELESS SYRINGE

(75) Inventors: Dahyabhai R. Patel, Laguna Niguel; John Michael Kay, Lake Forest, both of CA (US)

(73) Assignee: Jet Medica, L.L.C., Irvine, CA (US)

( * ) Notice: Subject to any disclaimer, the term of this patent is extended or adjusted under 35 U.S.C. 154(b) by 0 days.

(21) Appl. No.: 09/489,102

(22) Filed: Jan. 21, 2000

(51) Int. Cl.$^7$ .................................................. A61M 5/30
(52) U.S. Cl. .................................................................. 604/68
(58) Field of Search ........................... 604/110, 68, 140, 604/69, 141, 70, 143, 71, 145, 72, 148, 207, 210, 232, 187, 198, 200, 201–205; 128/DIG. 12

(56) References Cited

U.S. PATENT DOCUMENTS

| | | |
|---|---|---|
| 24,419 | 6/1859 | Veal . |
| 2,398,544 | 4/1946 | Lockhart ............................... 128/215 |
| 2,547,099 | 4/1951 | Smoot .................................. 128/173 |
| 2,605,763 | 8/1952 | Smoot .................................. 128/173 |
| 2,642,062 | 6/1953 | May ...................................... 128/173 |
| 2,645,223 | 7/1953 | Lawshe et al. ....................... 128/173 |
| 2,650,591 | 9/1953 | Love .................................... 128/173 |
| 2,691,374 | 10/1954 | McKibbin et al. .................. 128/272 |
| 2,699,166 | 1/1955 | Dickinson, Jr. et al. ............ 128/173 |
| 2,704,543 | 3/1955 | Scherer ................................ 128/173 |
| 2,737,946 | 3/1956 | Hein, Jr. .............................. 128/173 |
| 2,762,369 | 9/1956 | Venditty .............................. 128/173 |
| 2,762,370 | 9/1956 | Venditty .............................. 128/173 |
| 2,764,977 | 10/1956 | Ferguson ............................. 128/173 |
| 2,800,903 | 7/1957 | Smoot .................................. 128/173 |
| 2,821,193 | 1/1958 | Ziherl et al. ........................ 128/173 |
| 2,821,981 | 2/1958 | Ziherl et al. ........................ 128/173 |
| 2,902,994 | 9/1959 | Scherer ................................ 128/173 |
| 3,045,659 | 7/1962 | Malcolm .............................. 124/11 |
| 3,057,349 | 10/1962 | Ismach ................................ 128/173 |
| 3,115,133 | 12/1963 | Morando ............................. 128/173 |
| 3,131,692 | 5/1964 | Love .................................... 128/173 |
| 3,138,157 | 6/1964 | Ziherl et al. ........................ 128/173 |
| 3,202,151 | 8/1965 | Kath ..................................... 128/173 |
| 3,292,621 | 12/1966 | Banker ................................. 128/173 |
| 3,292,622 | 12/1966 | Banker ................................. 128/173 |

(List continued on next page.)

*Primary Examiner*—Manuel Mendez
(74) *Attorney, Agent, or Firm*—Kit M. Stetina; Stetina Brunda Garred & Brucker

(57) ABSTRACT

A single use needless syringe for administering a fluid medication. The syringe comprises a hollow, tubular body which includes a gas storage portion defining a storage chamber containing a quantity of pressurized gas. The body also includes an ejector portion defining a piston chamber which is selectively placeable into fluid communication with the storage chamber and has a piston movably disposed therein. In addition to the gas storage and ejector portions, the body has a barrel portion defining a delivery chamber for receiving a prescribed dosage of the fluid medication, with the delivery chamber being oriented relative to the piston chamber such that the piston is advanceable into the delivery chamber. A discharge orifice of the body fluidly communicates with the delivery chamber and allows the fluid medication to be filled thereinto and expelled therefrom. The syringe further comprises a fracturable release member which is disposed within the body and normally prevents the flow of the compressed gas from the storage chamber into the piston chamber. Removably attachable to the body is a trigger mechanism of the syringe which includes a stem portion partially insertable into the body and engagable to the release member, and a head portion attached to the stem portion. The application of compressive pressure to the head portion subsequent to the insertion of the stem portion into the body facilitates the fracture of the release member and resultant flow of the pressurized gas into the piston chamber. The compressed gas acts against the piston in a manner forcing the piston into the delivery chamber which causes the fluid medication to be expelled therefrom via the discharge orifice.

29 Claims, 4 Drawing Sheets

U.S. PATENT DOCUMENTS

| | | | |
|---|---|---|---|
| 3,355,722 | 11/1967 | Grubb et al. | 340/173 |
| 3,388,007 | 6/1968 | Fiandt | 136/166 |
| 3,461,867 | 8/1969 | Zimmet et al. | 128/173 |
| 3,464,412 | 9/1969 | Schwartz | 128/218 |
| 3,507,276 | 4/1970 | Burgess | 128/173 |
| 3,688,765 | 9/1972 | Gasaway | 128/173 H |
| 3,695,266 | 10/1972 | Lussier | 128/173 H |
| 3,714,943 | 2/1973 | Yanof et al. | 128/173 H |
| 3,788,315 | 1/1974 | Laurens | 128/173 H |
| 3,805,783 | 4/1974 | Ismach | 128/173 H |
| 3,815,594 | 6/1974 | Doherty | 128/173 H |
| 3,853,125 | 12/1974 | Clark et al. | 128/173 H |
| 3,859,996 | 1/1975 | Mizzy et al. | 128/173 H |
| 3,908,651 | 9/1975 | Fudge | 128/173 H |
| 3,933,155 | 1/1976 | Johnston | 128/173 H |
| 3,945,379 | 3/1976 | Pritz et al. | 128/173 H |
| 3,945,383 | 3/1976 | Bennett et al. | 128/272 |
| 4,004,575 | 1/1977 | Sarstedt | 127/2 F |
| 4,031,889 | 6/1977 | Pike | 128/215 |
| 4,059,107 | 11/1977 | Irigcuchi | 128/173 |
| 4,089,334 | 5/1978 | Schwebel et al. | 128/173 H |
| 4,103,684 | 8/1978 | Ismach | 128/173 H |
| 4,124,024 | 11/1978 | Schwebel et al. | 128/173 H |
| 4,128,098 | 12/1978 | Bloom et al. | 128/272.3 |
| 4,165,739 | 8/1979 | Doherty et al. | 128/173 H |
| 4,301,795 | 11/1981 | Zimmermann | 128/207.25 |
| 4,329,988 | 5/1982 | Sarnoff et al. | 128/218 F |
| 4,342,310 | 8/1982 | Lindmayer et al. | 128/207.25 |
| 4,378,015 | 3/1983 | Wardlaw | 128/218 F |
| 4,400,172 | 8/1983 | Dettbarn et al. | 604/70 |
| 4,403,609 | 9/1983 | Cohen | 604/70 |
| 4,403,989 | 9/1983 | Christensen et al. | 604/137 |
| 4,421,508 | 12/1983 | Cohen | 604/70 |
| 4,475,905 | 10/1984 | Himmelstrup | 604/208 |
| 4,518,385 | 5/1985 | Lindmayer et al. | 604/68 |
| 4,592,742 | 6/1986 | Landau | 604/71 |
| 4,596,556 | 6/1986 | Morrow et al. | 604/70 |
| 4,643,721 | 2/1987 | Brunet | 604/191 |
| 4,676,781 | 6/1987 | Phillips et al. | 604/135 |
| 4,680,027 | 7/1987 | Parsons et al. | 604/68 |
| 4,722,728 | 2/1988 | Dixon | 604/68 |
| 4,874,367 | 10/1989 | Edwards | 604/72 |
| 4,913,699 | 4/1990 | Parsons | 604/68 |
| 4,941,880 | 7/1990 | Burns | 604/143 |
| 5,009,634 | 4/1991 | Feldman | 604/27 |
| 5,009,637 | 4/1991 | Newman et al. | 604/68 |
| 5,024,656 | 6/1991 | Gasaway et al. | 604/70 |
| 5,026,343 | 6/1991 | Holzer | 604/68 |
| 5,062,830 | 11/1991 | Dunlap | 604/68 |
| 5,064,413 | 11/1991 | McKinnon et al. | 604/70 |
| 5,085,641 | 2/1992 | Sarnoff et al. | 604/134 |
| 5,190,523 | 3/1993 | Lindmayer | 604/72 |
| 5,480,381 | 1/1996 | Weston | 604/68 |
| 5,499,972 | 3/1996 | Parsons | 604/68 |
| 5,593,388 | 1/1997 | Phillps | 604/135 |
| 5,851,198 | 12/1998 | Castellano et al. | 604/68 |

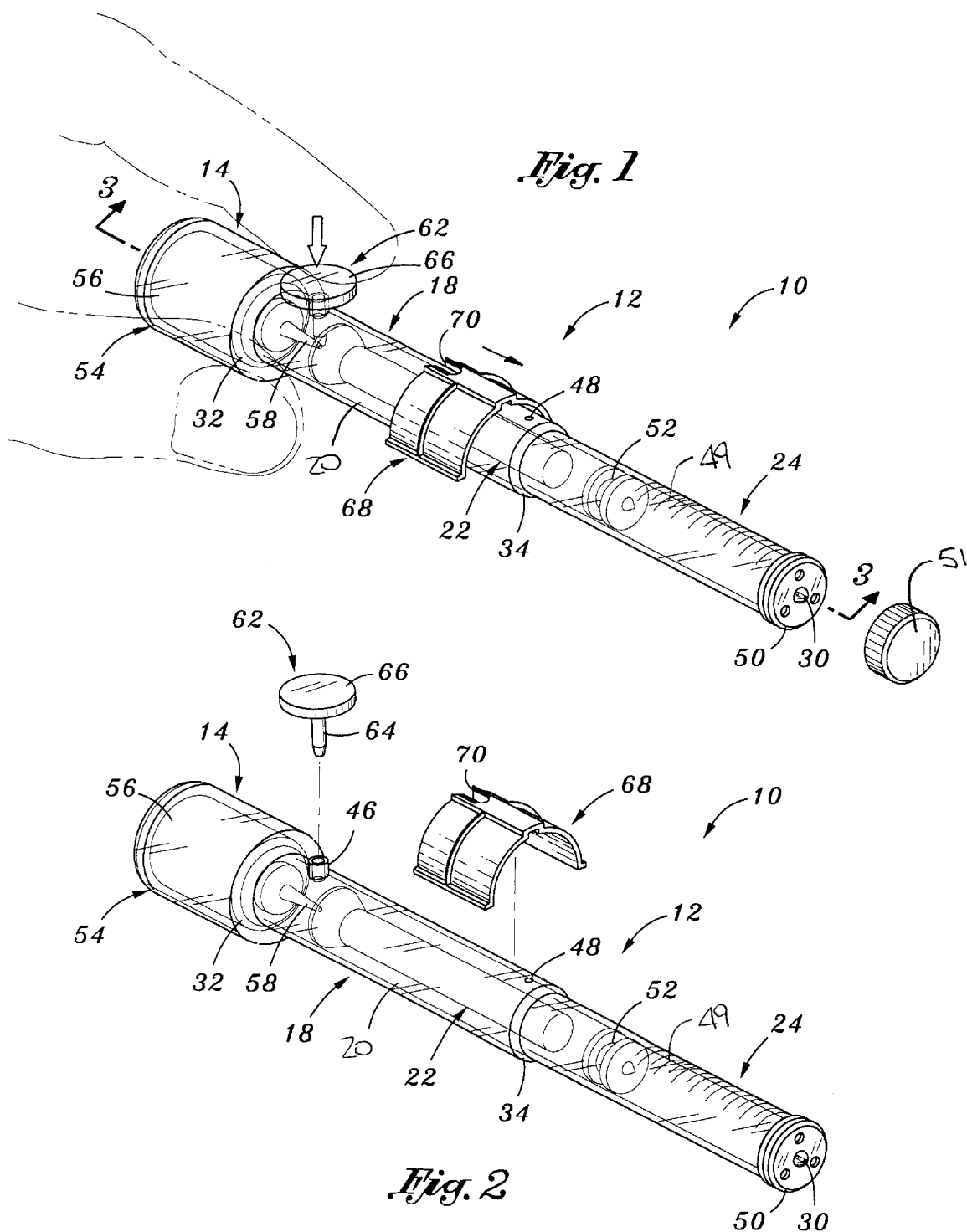

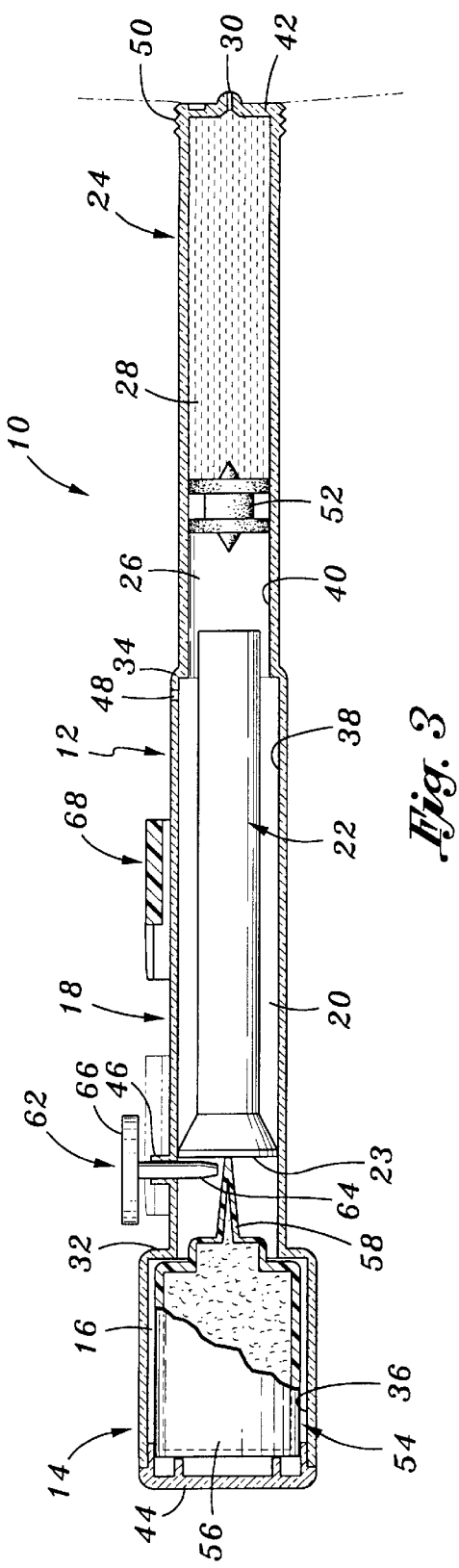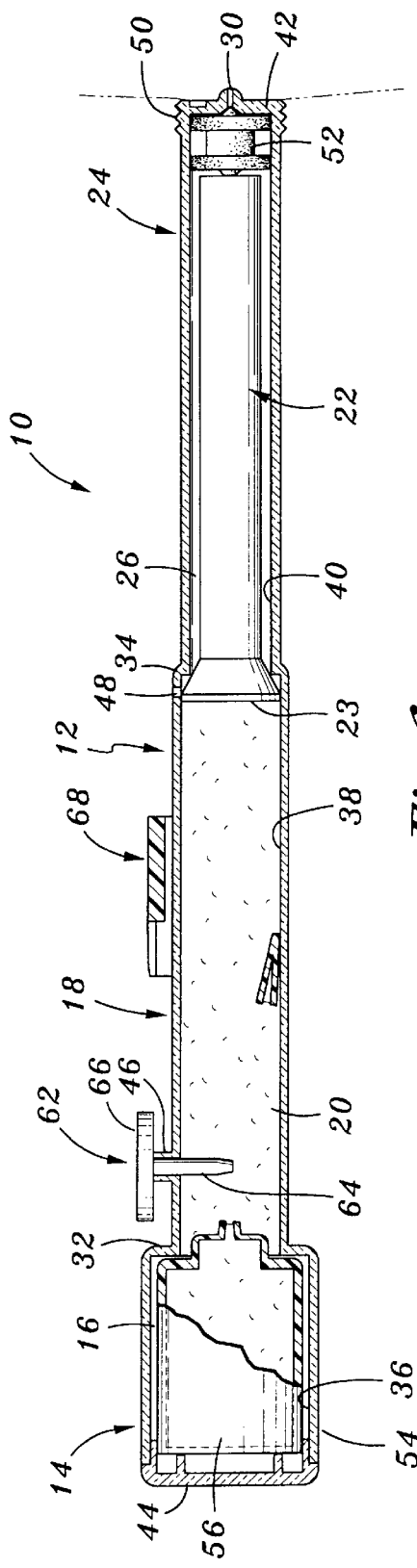

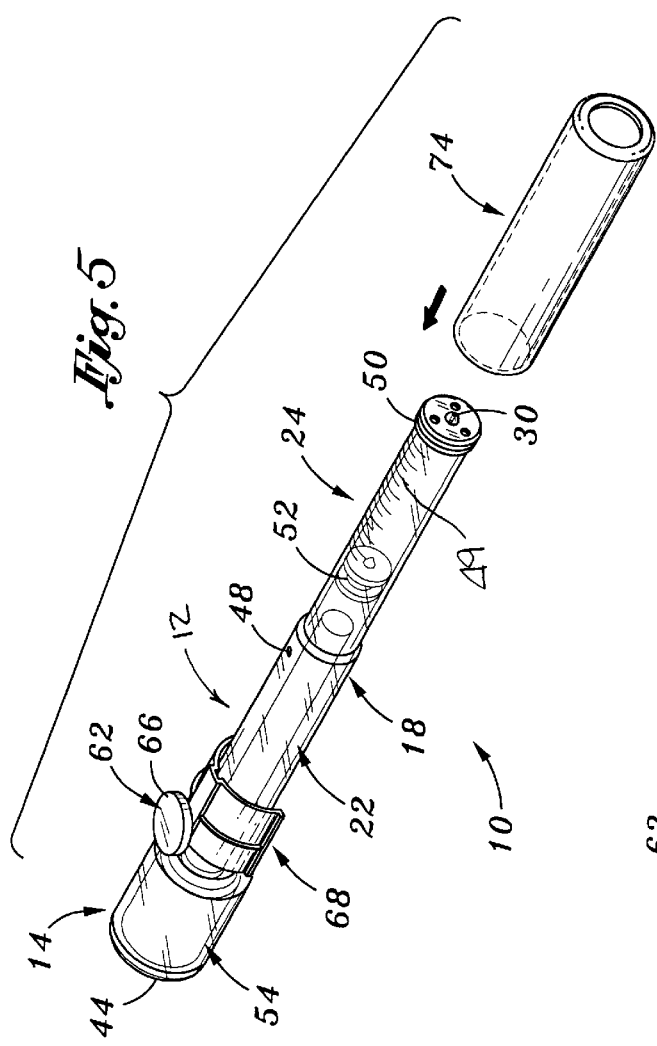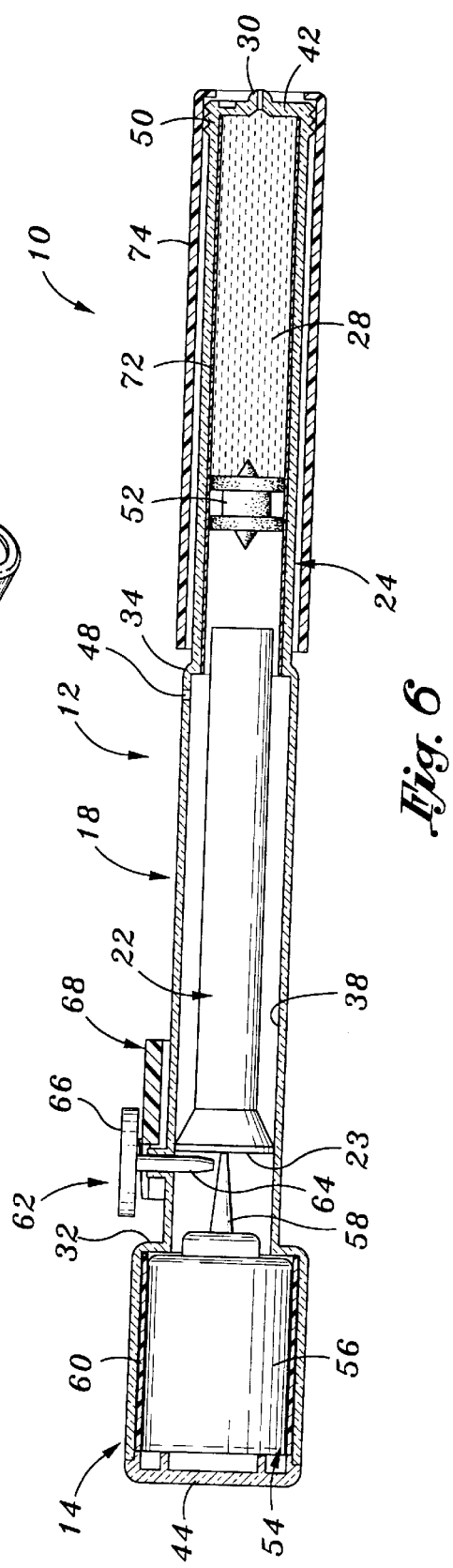

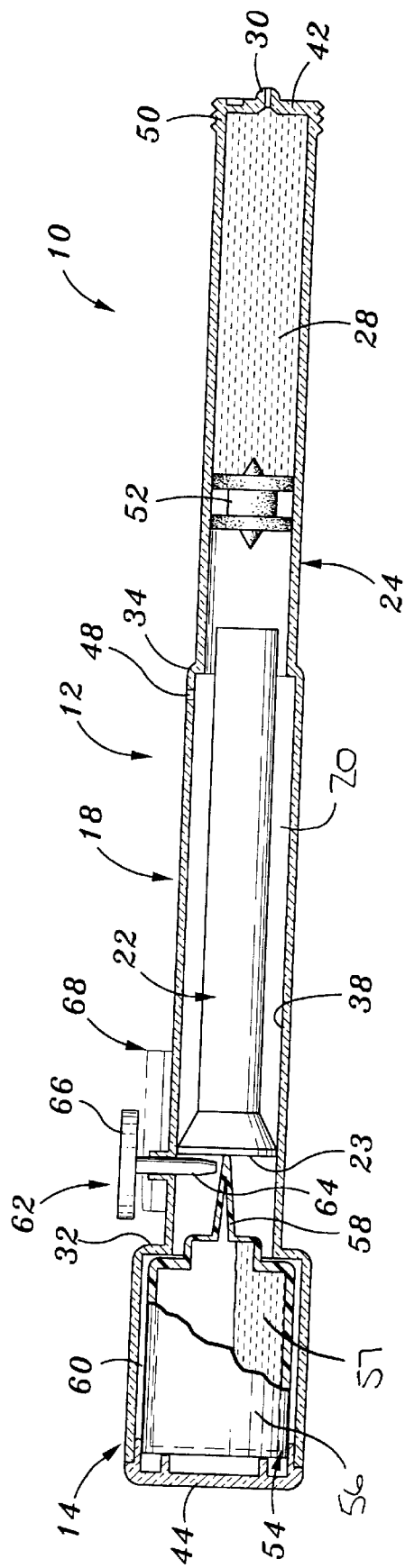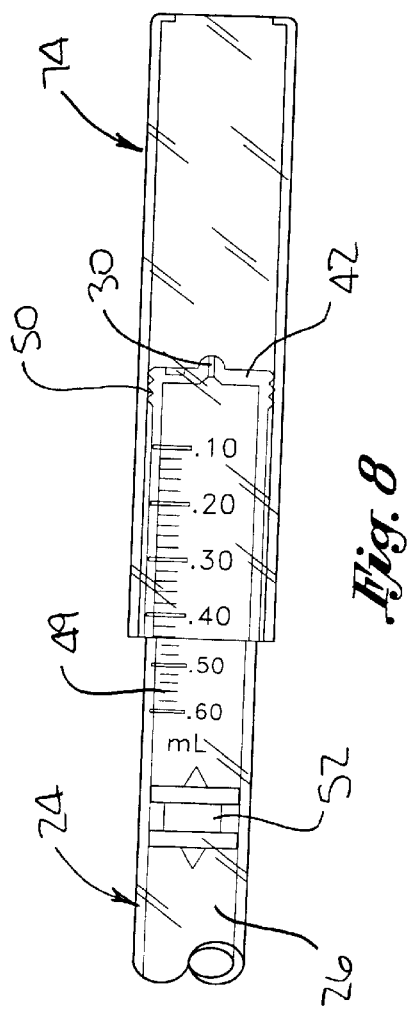
Fig. 7
Fig. 8

NEEDLELESS SYRINGE

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates generally to hypodermic injection devices, and more particularly to a gas pressurized, single-use needleless injection device or syringe that avoids piercing the skin by utilizing a high pressure jet to pass a medication or other substance through the skin.

In the medical profession, it is known to administer needleless medication injections through the use of "permanent gun" instruments which are generally referred to as "jet injectors". These prior art devices typically employ the use of either a compression spring or a compressed inert gas to propel fluid medication via a push rod plunger through a small orifice or opening of an injector nozzle. The injector nozzle is pressed directly against the injection site in perpendicular relation thereto, with the fluid medication generally being accelerated at a high rate of speed of between about 800 feet per second and 1,200 feet per second. This rate of speed causes the fluid medication to pierce through the skin's surface without the use of a needle, thus resulting in the fluid medication being deposited in a flower-like pattern under the skin's surface. This method of medication delivery is typically referred to in the medical profession as a subcutaneous injection. The jet injectors and similar needleless injection devices are generally perceived as reducing the relative risk and discomfort of puncturing the epidermis with a hypodermic needle, and being more easily used by persons of limited skill. Thus, the use of such devices has become of increasing interest, particularly by users such as those requiring frequent insulin injections.

Conventional jet injectors as known in the prior art are often cumbersome and awkward to use, with the preparation of a typical, reusable jet injector for administering an injection requiring several steps. More particularly, prior to each injection, the injector nozzle must be sterilized. To satisfy this need, the user removes the injector nozzle from the jet injector and boils the nozzle in water to assure a reasonable degree of sterilization. After the injector nozzle has been cleaned and sterilized, the user replaces it on the jet injector and prepares the same for loading the medication which is to be injected into the skin. A concern often associated with the injector nozzle in the prior art reusable jet injectors is that due to the relatively small opening (approximately 0.004 inches or less), the nozzle has a tendency to clog if the jet injector is left unused for a period of time or if the user does not clean the nozzle each time after its use and prior to its reuse.

A further deficiency of prior art jet injectors is that loading the same with fluid medication is typically a time consuming and delicate operation. In a typical loading procedure, an adaptor which contains a needle is first placed through the rubber septum of a medication vial. The injector nozzle of the jet injector is then mated or coupled to the adaptor, with the user then proceeding to draw medication into the delivery chamber of the jet injector. This operation may repeated several times, until the trapped air in the delivery chamber is removed. When this pre-injection operation is complete, the user selects an injection site on the skin and administers the injection.

However, a used and worn delivery orifice of the injector nozzle can slow down the delivery speed of the injected fluid medication, thus resulting in inadequate penetration and bruising of the skin at the injection site. Additionally, the improper use of jet injectors creates bruising (subdermal hematoma) when the injector nozzle is not firmly pressed against the skin at the injection site. Bruising may also occur if the orifice or opening of the injector nozzle is partially clogged or worn out.

With regard the prior art jet injectors employing the use of a compression spring, such compression spring propelled jet injectors are typically considered deficient in that they do not offer linear delivery speeds, i.e., a constant speed of the fluid medication being injected. Moreover, spring propelled jet injectors with weak or deteriorated springs often slow down the delivery speed of the fluid medication while the same is being administered into the skin which can result in improper fluid penetration. Reduced speed of the fluid medication delivery can also cause improper dosing and bruising at the injection site.

In recognition of the aforementioned deficiencies of jet injectors, there has been developed in the prior art single use needless injection devices or syringes, with one such injection device being described in U.S. Pat. No. 4,913,699 issued to Parsons on Apr. 3, 1990 which is owned by the Applicant. More particularly, the Parsons reference discloses a pre-sterilized disposable, single-use injection device which has its own compressed gas power source and is small and light enough for the user to carry the device along during the day. The Parsons injection device is adapted to be filled with a selected dosage of fluid medication from existing medication vials, and is operable without the need to cock a spring due to its use of compressed gas as the source of power.

Though the Parsons injection device overcomes many of the deficiencies of the prior art jet injectors, it possesses its own deficiencies which detract from its overall utility. More particularly, the configuration of the trigger mechanism of the Parsons injection device makes it susceptible to accidental discharge during manufacture/assembly and transport, in addition to increasing the complexity of the manufacturing and assembly process and hence the cost thereof. Moreover, the Parsons injection device lacks a quickly and easily discernable visual indicator that the compressed gas power source has been discharged. Also, the Parsons injection device is not well suited to being pre-filled with a fluid medication since it is neither outfitted with structures or fabricated from materials which are adapted to extend the shelf life thereof by maintaining the bioavailability of the fluid medication, or reducing leakage or outgassing of the pressurized gas.

The needleless syringe constructed in accordance with the present invention is a single unit, single use syringe which is non-reusable and completely disposable, thus minimizing its susceptibility to contamination. The present needleless syringe overcomes the deficiencies of the Parsons injection device by providing a trigger mechanism specifically configured to facilitate the manufacture, assembly, pre-filling and transport of the syringe with substantially reduced susceptibility to accidental actuation or discharge. Additionally, the present needleless syringe may be provided with internal liners or sleeves specifically adapted to increase the shelf life thereof by substantially reducing the potential leakage of pressurized gas therefrom and/or maintaining the bioavailability of the fluid medication by preventing a derogatory interaction between the fluid medication and the syringe material or protecting the fluid medication from exposure to air and/or sunlight (i.e., ultraviolet radiation) if photosensitive. The present needleless syringe may be provided with an external reinforcement sleeve which allows for the fabrication of the syringe from lower strength materials specifically suited to maintain the bioavailability of the fluid medication. Various coatings may also be applied to distinct sections of the interior of the needleless syringe which change colors when exposed to the pressurized gas for purposes of providing a clear visual indication that the same has been discharged. These, as well as other features and advantages of the present invention, will be discussed in more detail below.

BRIEF SUMMARY OF THE INVENTION

In accordance with the present invention, there is provided a single use needleless syringe for administering a fluid medication. In the preferred embodiment, the syringe comprises a hollow, tubular body which itself includes a gas storage portion defining a storage chamber containing a quantity of a compressed gas. A preferred compressed gas used in the present syringe is carbon dioxide. In addition to the gas storage portion, the body of the syringe includes an ejector portion defining a piston chamber which is selectively placeable into fluid communication with the storage chamber and has a piston movably disposed therein. Also included in the body is a barrel portion defining a delivery chamber for receiving a prescribed dosage or quantity of the fluid medication, and a discharge orifice which is in fluid communication with the delivery chamber for allowing the fluid medication to be filled thereinto and expelled or ejected therefrom. In the body of the syringe, the delivery chamber is oriented relative to the piston chamber such that the piston is advanceable into the delivery chamber. Preferably disposed within the delivery chamber is a plunger member which prevents the fluid medication filled into the delivery chamber from flowing or migrating into the piston chamber.

The syringe of the present invention further comprises a fracturable release member which is disposed within the body and, prior to its fracture, prevents the flow of the compressed gas from the storage chamber into the piston chamber. Also included in the syringe is a trigger mechanism which is removably attachable to the body. The trigger mechanism itself comprises a stem portion which is partially insertable into the body and engagable to the release member. In addition to the stem portion, the trigger mechanism includes a head portion which is attached to the stem portion, and preferably integrally connected thereto.

In the operation of the needless syringe of the present invention, the application of compressive pressure to the head portion of the trigger mechanism subsequent to the insertion of the stem portion thereof into the body facilitates the fracture or breakage of the release member and resultant flow of the pressurized gas into the piston chamber. The compressed gas acts against the piston in a manner forcing the piston into the delivery chamber which causes the fluid medication to be expelled therefrom via the discharge orifice.

In the preferred embodiment of the present invention, the gas storage, ejector and barrel portions of the syringe body each have a generally circular cross-sectional configuration, with the storage, piston and delivery chambers defined thereby being disposed in coaxial alignment with each other.

The body is preferably formed such that the diameter of the gas storage portion exceeds the diameter of the ejector portion, with the diameter of the ejector portion exceeding the diameter of the barrel portion. The source of compressed gas is preferably a compressed gas cartridge which is disposed within the gas storage portion of the body. The release member preferably comprises an integrally formed portion of the compressed gas cartridge, and more particularly an elongate quill thereof which extends axially into the piston chamber. The stem portion of the trigger mechanism is radially insertable into the ejector portion of the body so as to extend in generally perpendicular relation to the quill of the compressed gas cartridge. As a result, the application of compressive pressure to the head portion of the trigger mechanism subsequent to the insertion of the stem portion into the ejector portion of the body causes the stem portion to act against the quill in a manner which fractures the same and results in the flow of the compressed gas from the compressed gas cartridge into the piston chamber.

Since the trigger mechanism of the present needleless syringe is removably attachable to the body thereof, the syringe is well suited to being pre-filled with the fluid medication due to the reduced susceptibility thereof to accidental actuation or discharge during the process of manufacture, assembly, filling, and transport. Though the attachment of the trigger mechanism to the body can be deferred until the syringe is ready for use, the syringe is further preferably provided with a safety member which prevents the actuation of the trigger mechanism when the same is releasably attached to the body. The safety member has an arcuate configuration, and is slidably attached to the ejector portion of the body. The safety member has a slot formed therein, and is preferably sized to circumvent slightly greater than one-half the circumference of the ejector portion so as to be maintainable in engagement thereto. The safety member is movable back and forth along the ejector portion between locked and unlocked positions. When moved to the locked position, the stem portion is received into the slot and prevented from radial movement by the engagement of the head portion to the safety member itself. When the safety member is moved to the unlocked position, the application of compressive pressure to the head portion facilitates the radial movement of the stem portion towards the quill and fracture thereof by the force of the stem portion acting thereagainst.

In the present syringe, the body includes an outer surface and an inner surface having a proximal section which defines the storage chamber, an intermediate section which defines the piston chamber, and a distal section which defines the delivery chamber. The outer surface of the barrel portion of the body which defines the delivery chamber preferably includes measurement indicia applied thereto. The syringe further preferably comprises a reactive coating which is applied to the intermediate section of the inner surface and adapted to change color when exposed to the compressed gas flowing from the storage chamber into the piston chamber upon the fracture of the release member (i.e., the quill of the compressed gas cartridge) by the trigger mechanism. This reactive coating provides a quickly and easily discernable visual indication that the fluid medication has been discharged from the syringe. When the body is provided with the reactive coating, the same is preferably fabricated from a transparent or translucent material.

The compressed gas of the present syringe, which is preferably carbon dioxide, is preferably stored within the compressed gas cartridge in a liquified form. In addition or as an alternative to the body being provided with the above-described reactive coating, the compressed gas cartridge may be fabricated from a transparent or a semi-transparent material, thus allowing for the visual observation of the liquified compressed gas therein. The absence of the appearance of the liquified compressed gas within the compressed gas cartridge provides an indication that the syringe has been actuated, or has exceeded its shelf life in a manner resulting in all of the compressed gas being out-gassed therefrom. As will be recognized, when the transparent or semi-transparent compressed gas cartridge is provided in the present syringe, the body thereof is preferably fabricated from a transparent material.

The syringe may also be provided with a liner or sleeve which is disposed within the storage chamber and extends along the proximal section of the inner surface for preventing leakage or out-gassing of the compressed gas from within the storage chamber. A liner may also be disposed within the delivery chamber and extended along the distal section of the inner surface for maintaining the bioavailability of the fluid medication filled into the delivery chamber. This particular liner may be fabricated from an inert material which prevents interaction between the fluid medication and the material of the body, protects the fluid medication from exposure to air in the event the body material is permeable, and/or protects the fluid medication from exposure to ultraviolet radiation in the event it is photosensitive.

As an alternative to the use of the liner or sleeve within the delivery chamber of the body, the body itself may be fabricated from a material which is specifically suited to maintain the bioavailability of the fluid medication pre-filled into the delivery chamber, and thus extend the shelf life of the present syringe. In this respect, the selected material for the body of the syringe may be one which prevents the exposure of the fluid medication to ultraviolet radiation, is of low permeability to prevent the exposure of the fluid medication to air, or is inert to prevent any derogatory interaction with the fluid medication. In the event such selected material is of relatively low strength as could increase its susceptibility to bursting upon the fracture of the quill and release of the compressed gas into the piston chamber, the present syringe may be provided with an external, tubular reinforcement sleeve which is advanceable over the outer surface of the barrel portion of the body. The reinforcement sleeve is preferably cylindrically configured and formed such that when advanced over the barrel portion, it does not interfere with the engagement of the discharge orifice to the injection site on the user's skin. The sleeve may be fabricated from a material which magnifies the measurement indicia disposed on the barrel portion when advanced thereover.

Further in accordance with the present invention, there is provided a method of administering a needleless injection comprising the initial step of providing a needleless syringe having the above-described structural features. The syringe is preferably pre-filled with the fluid medication. The trigger mechanism is then attached to the body by partially inserting the stem portion thereof into the body. Thereafter, compressive pressure is applied to the head portion of the trigger mechanism to facilitate the fracture of the release member and resultant flow of the pressurized gas into the piston chamber.

BRIEF DESCRIPTION OF THE DRAWINGS

These, as well as other features of the present invention, will become more apparent upon reference to the drawings wherein:

FIG. 1 is a perspective view of the needleless syringe constructed in accordance with the present invention;

FIG. 2 is an exploded view of the needleless syringe shown in FIG. 1, illustrating the trigger mechanism and lock member thereof;

FIG. 3 is a cross-sectional view taken along line 3—3 of FIG. 1;

FIG. 4 is a cross-sectional view similar to FIG. 3, illustrating the present needleless syringe subsequent to the discharge of fluid medication therefrom;

FIG. 5 is an exploded view of an alternative embodiment of the present needleless syringe including an external reinforcement sleeve;

FIG. 6 is a cross-sectional view of the alternative embodiment of the needleless syringe shown in FIG. 5, illustrating the reinforcement sleeve operatively positioned thereupon;

FIG. 7 is a cross-sectional view of a further alternative embodiment of the present needleless syringe including a transparent or semi-transparent compressed gas cartridge allowing for the visual observation of the liquified compressed gas therein; and FIG. 8 is a partial side-elevational view illustrating the manner in which the reinforcement sleeve shown in FIGS. 5 and 6 magnifies the measurement indicia preferably disposed on the body of the needleless syringe.

DETAILED DESCRIPTION OF THE INVENTION

Referring now to the drawings wherein the showings are for purposes of illustrating a preferred embodiment of the present invention only, and not for purposes of limiting the same, FIGS. 1 and 2 illustrate the needleless syringe 10 constructed in accordance with the preferred embodiment of the present invention. As indicated above, the present invention constitutes an improvement over the device described in U.S. Pat. No. 4,913,699, the disclosure of which is incorporated herein by reference. The needleless syringe 10 of the present invention is a single unit, single use device, which is intended to be non-reusable and completely disposable, thus substantially eliminating its susceptibility to contamination.

Referring now to FIGS. 1–4, the syringe 10 comprises a hollow, tubular body 12, the preferred materials for which will be discussed in more detail below. The body 12 includes a gas storage portion 14 which defines a storage chamber 16. In addition to the gas storage portion 14, the body 12 includes an ejector portion 18 defining a piston chamber 20 which is selectively placeable into fluid communication with the storage chamber 16 and has an elongate piston 22 movably disposed therein. The piston 22 itself defines an enlarged face 23 on one end thereof. Also included in the body 12 is a barrel portion 24 defining a delivery chamber 26 for receiving a prescribed dosage or quantity of a fluid medication 28 (as seen in FIG. 3), and a discharge orifice 30 which is in fluid communication with the delivery chamber 26 for allowing the fluid medication 28 to be filled thereinto and expelled or ejected therefrom.

In the syringe 10, the gas storage, ejector and barrel portions 14, 18, 24 of the body 12 each have a generally circular cross-sectional configuration, with the storage, piston and delivery chambers 16, 20, 26 defined thereby being disposed in coaxial alignment with each other. The body 12 is preferably formed such that the diameter of the gas storage portion 14 exceeds the diameter of the ejector portion 18, with the diameter of the ejector portion 18 exceeding the diameter of the barrel portion 24. In this regard, the gas storage portion 14 transitions into the ejector portion 18 at a first annular shoulder 32, with the ejector portion 18 transitioning into the barrel portion 24 at a second annular shoulder 34. As is apparent from FIGS. 1–4, in the body 12 of the syringe 10, the delivery chamber 26 is oriented relative to the piston chamber 20 such that the piston 22 is advanceable into the delivery chamber 26.

As is best seen in FIGS. 3 and 4, the barrel portion 24 of the body 12 includes an end wall 42 which defines the distal end of the syringe 10 and has the discharge orifice 30 formed therein. Additionally, attached to the body 12 is an end cap 44 which defines the proximal end of the syringe 10. The body 12 further defines an outer surface and an inner surface having a proximal section 36, an intermediate section 38, and a distal section 40. The proximal section 36 and inner surface of the end cap 44 collectively define the storage chamber 16, with the intermediate section 38 defining the piston chamber 20 and the distal section 40 (including the inner surface of the end wall 42) defining the delivery chamber 26. Integrally connected to and extending radially from the outer surface of the ejector portion 18 of the body 12 in relative close proximity to the first shoulder 32 is a tubular projection 46 which communicates with the piston chamber 20. Additionally, disposed within the ejector portion 18 of the body 12 is a vent aperture 48 which fluidly communicates with the piston chamber 20. The use of the projection 46 and vent aperture 48 will be described in more detail below. Preferably disposed on or applied to the outer surface of the barrel portion 24 of the body 12 and extending axially therealong is measurement indicia 49 for use in accurately determining the amount of fluid medication 28 filled into the delivery chamber 26.

A portion of the outer surface of the barrel portion 24 of the body 12 adjacent the end wall 42 (i.e., adjacent the distal end of the syringe 10) may be formed to include external threads 50 for purposes of allowing the threadable engagement of a protective cap 51 to the body 12. As will be recognized, this protective cap 51 is used to shield the discharge orifice 30 for purposes of maintaining the sterility thereof. Upon the removal of this protective cap 51 from the body 12, the external threads 50 may also be used to facilitate the threadable engagement of a loader mechanism (not shown) to the body 12 for purposes of filling the delivery chamber 26 with the fluid medication 28. To maintain the fluid medication within the delivery chamber 26 when filled thereinto, the syringe 10 is provided with a plunger member 52 which is disposed within the delivery chamber 26 and prevents the flow or migration of the fluid medication 28 into the piston chamber 20. The plunger member 52 is preferably fabricated from an inert, rubber material, and is sized and configured so as to maintain a sliding seal with the distal section 40 of the inner surface of the body 12. Additionally, at least one face of the plunger member 52 is formed to conform to the shape of the delivery chamber 26 at the discharge orifice 30 so that no fluid medication 28 remains within the delivery chamber 26 upon the actuation of the syringe 10.

The syringe 10 of the present invention is provided with a source of compressed gas which facilitates the movement of the piston 22 from within the piston chamber 20 into the delivery chamber 26 for purposes of expelling or discharging the fluid medication 28 from therewithin. The source of the compressed gas is preferably a compressed gas cartridge 54 which is disposed within the gas storage portion 14 of the body 12, and more particularly the storage chamber 16. The compressed gas cartridge 54 includes a cylindrically configured body portion 56 and an elongate quill 58 which is integrally connected to the body portion 56 and protrudes axially from one end thereof. Disposed within the compressed gas cartridge 54 is a quantity of compressed gas which is preferably carbon dioxide. The compressed gas cartridge 54 is inserted into the storage chamber 16 prior to the attachment of the end cap 44 to the body 12.

The body portion 56 is preferably sized and configured such that when inserted into the storage chamber 16, the attachment of the end cap 44 to the body 12 will facilitate the compression of the body portion 56 between an annular flange of the end cap 44 and the inner surface of the first shoulder 32, thus fixedly securing the compressed gas cartridge 54 within the gas storage portion 14. When the compressed gas cartridge 54 is properly positioned within the storage chamber 16 of the gas storage portion 14, the quill 58 extends or protrudes axially into the piston chamber 20. As will also be discussed in more detail below, the quill 58 of the compressed gas cartridge 54 is selectively fracturable and, when fractured, releases the compressed gas from within the body portion 56. Thus, the quill 58 defines a fracturable release member of the syringe 10 which, prior to its fracture, normally prevents the flow of the compressed gas from within the storage chamber 16 (i.e., from within the body portion 56 of the compressed gas cartridge 54) into the piston chamber 20.

Referring now to FIG. 6, the syringe 10 may be provided with a liner or sleeve 60 which is disposed within the storage chamber 16 and extends along the proximal section 36 of the inner surface of the body 12. The liner 60 is preferably sized such that when disposed within the storage chamber 16, it is firmly seated between the proximal section 36 and the outer surface of the body portion 56 of the compressed gas cartridge 54. The purpose of the liner 60 is to prevent any leakage or out-gassing of the compressed gas from within the storage chamber 16, as could occur over time as a result of the permeability of the material used to fabricate the compressed gas cartridge 54. In this respect, the liner 60 is used to maintain the "potency" of the compressed gas supply for the syringe 10, thus extending the shelf life thereof.

The syringe 10 of the present invention further comprises a trigger mechanism 62 which is removably attachable to the body 12, and more particularly the ejector portion 18 thereof. The trigger mechanism 62 itself includes an elongate stem portion 64 having an enlarged head portion 66 integrally formed on one end thereof. The stem portion 64 is insertable into the projection 46 and advanceable into the piston chamber 20 in the manner best seen in FIGS. 3 and 6. The advancement of the stem portion 64 into the piston chamber 20 is limited by the engagement of the end thereof opposite that including the head portion 66 formed thereon to the quill 58 of the compressed gas cartridge 54. Due to the protrusion of the projection 46 radially from the ejector portion 18 and the axial extension of the quill 58 into the piston chamber 20, the stem portion 64 extends generally perpendicularly relative to the quill 58 when advanced into the piston chamber 20 via the projection 46.

As is further seen in FIGS. 3 and 6, the stem portion 64 of the trigger mechanism 62 is sized such that when one end thereof is engaged to the quill 58, a gap is defined between the head portion 66 and the distal end of the projection 46. As a result, the application of compressive pressure to the exposed outer surface of the head portion 66 will facilitate the inward radial movement of the stem portion 64, with such movement being limited by the abutment of the head portion 66 against the projection 46. Such inward radial movement causes the stem portion 64 to exert a force, i.e., a moment, against the quill 58 in an amount sufficient to facilitate the fracture or breakage of the same. As indicated above, such fracture of the quill 58 facilitates the immediate release or flow of the compressed gas from within the body portion 56 into the piston chamber 20.

Since the trigger mechanism 62 of the syringe 10 is removably attachable to the body 12 thereof, the syringe 10 is well suited to being pre-filled with the fluid medication 28 due to the reduced susceptibility of the syringe 10 to accidental actuation or discharge during the process of manufacture, assembly, filling, and transport. Though the attachment of the trigger mechanism 62 to the body 12 can be deferred until the syringe 10 is ready for use, the syringe 10 is further preferably provided with a safety member 68 which prevents the actuation of the trigger mechanism 62 when the same is releasably attached to the body 12. As is seen in FIGS. 1-6, the safety member 68 has an arcuate configuration, and is slidably attached to the ejector portion 18 of the body 12. The safety member 68 has a slot 70 formed therein, and is preferably sized to circumvent slightly greater than one-half of the circumference the ejector portion 18 so as to be maintainable in slidable engagement thereto. The safety member 68 is moveable back and forth along the ejector portion 18 between a locked position (shown in FIGS. 5 and 6) and an unlocked position (shown in FIGS. 1, 3 and 4). When the safety member 68 is in its locked position, the stem portion 64 of the trigger mechanism 62 and a portion of the projection 46 are received into the slot 70, with the stem portion 64 being prevented from radial movement by the engagement of the head portion 66 to the safety member 68 itself. When the safety member 68 is moved to its unlocked position, the application of compressive pressure to the head portion 66 of the trigger mechanism 62 facilitates the radial movement of the stem portion 64 toward the quill 58 and fracture thereof by the force of the stem portion 64 acting thereagainst as discussed above.

Referring now to FIG. 6, as indicated above, the liner 60 may be disposed within the storage chamber 16 for purposes of extending the shelf life of the syringe 10 by preventing leaking or out-gassing of compressed gas from the gas storage portion 14 of the body 12. A liner or sleeve 72 may also be disposed within the delivery chamber 26 and extended along the distal section 40 of the inner surface of the body 12 for purposes of maintaining the bioavailability of the fluid medication 28 filled into the delivery chamber 26. Though not shown in FIG. 6, the liner 72 may be formed such that it covers the inner surface of the end wall 42. The liner 72 may be fabricated from an inert material which prevents interaction between the fluid medication 28 and the material used to fabricate the body 12, protects the fluid medication 28 from exposure to air in the event the material of the body 12 is permeable, and/or protects the fluid medication 28 from exposure to ultraviolet radiation in the event it is photosensitive.

Having thus described the basic structural elements of the syringe 10, the preferred method of using the same will now be discussed with reference to FIGS. 1–6. As indicated above, the syringe 10 is preferably pre-filled with the fluid medication 28, though the same may alternatively be filled through the use of the aforementioned loader mechanism which is threadably engagable to the threads 50 of the body 12. Assuming the syringe 10 to be pre-filled, the use thereof is initiated by the removal of the protective cap 51 from the threads 50 of the body 12. Thereafter, the trigger mechanism 62 is attached to the body 12 by the insertion of the stem portion 64 thereof into the projection 46 in the above-described manner. Subsequent to the insertion of the stem portion 64 into the projection 46, the end wall 42, and in particular the discharge orifice 30 formed therein, is placed into firm abutting contact with the user's skin at the desired injection site. Compressive pressure is then applied to the head portion 66 of the trigger mechanism 62 by one of the fingers of the hand of the user in which the syringe 10 is being grasped. As indicated above, this application of compressive pressure facilitates the inward radial movement of the stem portion 64 which causes it to exert a force against and ultimately fracture the quill 58 of the compressed gas cartridge 54. The fracture of the quill 58 results in the flow of the compressed gas stored within the body portion 56 of the compressed gas cartridge 54 into the piston chamber 20. The gas acts against the enlarged face 23 of the piston 22 which causes the piston 22 to be driven from the piston chamber 20 into the delivery chamber 26 in the manner shown in FIG. 4. This action of the piston 22 causes the plunger member 52 to act against the fluid medication 28 in a manner forcing it out of the discharge orifice 30 as a high pressure jet. As the piston 22 moves toward the end wall 42 of the barrel portion 24, gas between the piston 22 and plunger member 52 vents through the vent aperture 48. The compressed gas is also discharged or vented between the stem portion 64 and the inner surface of the projection 46.

The enlarged face 23 of the piston 22 is preferably sized so as to have a larger surface area than the end face of the plunger member 52 against which the piston 22 acts during the discharge of the fluid medication 28 from the delivery chamber 26. This surface area differential results in more pressure being applied to the fluid medication 28 than the compressed gas applies to the face 23 of the piston 22. This pressure application may be utilized to achieve an injection pressure at the discharge orifice 30 of from about 2500–5000 psi, depending on the precise configuration employed, whereas the compressed gas may exhibit a pressure of about 840 psi at room temperature.

As indicated above, the safety member 68 may be included with the syringe 10 for purposes of preventing the accidental discharge thereof after the trigger mechanism 62 has been releasably attached to the body 12. In the event the safety member 68 is included with the syringe 10, the preferred method of using the syringe 10 includes the additional step of moving the safety member 68 from its locked position preventing the radial movement of the stem portion 64, to its unlocked position whereat the application of compressive pressure to the head portion 66 facilitates the fracture of the quill 58 by the force of the stem portion 64 acting thereagainst.

As is apparent from FIG. 4, visual indicators that the syringe 10 has been actuated and the fluid medication 28 discharged therefrom include the position of the piston 22 within the delivery chamber 26, and the fractured portion of the quill 58 being within the now vacant piston chamber 20. The syringe 20 may further be provided with a reactive coating which is applied to the intermediate section 38 of the inner surface of the body 12 and adapted to change color when exposed to the compressed gas flowing from the compressed gas cartridge 54 into the piston chamber 20 upon the fracture of the quill 58. Such reactive coating provides a quickly and easily discernable visual indication that the fluid medication 28 has been discharged from the syringe 10. When the body 12 is provided with such reactive coating, it is preferably fabricated from a transparent material. It is further contemplated that the material used to fabricate the body portion 56 of the compressed gas cartridge 54 is such that a color change is effectuated when the compressed gas is discharged from the compressed gas cartridge 54. As will be recognized, it is also preferable that the body 12 be fabricated from a transparent material if such color changing compressed gas cartridge 54 is employed in the syringe 10.

Referring now to FIG. 7, in the compressed gas cartridge 54 used in the present syringe 10, the compressed gas (e.g., carbon dioxide) is preferably stored within the body portion 56 in a liquified form. In FIG. 7, the liquified compressed gas is identified with the reference numeral 57. It is contemplated that in addition or as an alternative to the body 12 being provided with above-described reactive coating, the compressed gas cartridge 54 may be fabricated from a transparent or semi-transparent material so as to allow for the visual observation of the liquified compressed gas 57 therewithin. It will be recognized that if the compressed gas cartridge 54 is fabricated from the transparent or semi-transparent material, at least the gas storage portion 14 of the body 12 will be fabricated from a transparent material. When the compressed gas cartridge 54 is fabricated from the transparent or semi-transparent material, the absence of any visually observable liquified compressed gas 57 provides a visual indication that the syringe 10 has been actuated, or has exceeded its shelf life resulting in all of the liquified compressed gas 57 being outgassed from therewithin. It is further contemplated that the liquified compressed gas 57 may include a color or dye added thereto such that the expulsion or discharge thereof from within the compressed gas cartridge 54 will effectuate a color change within the ejector portion 18 of the body 12 defining the piston chamber 20.

As an alternative to the use of the liner 72 within the delivery chamber 26 of the body 12, the body 12 itself may be fabricated from a material which is specifically suited to maintain the bioavailability of the fluid medication 28 pre-filled into the delivery chamber 26, and thus extend the shelf life of the syringe 10. In this respect, the selected material for the body 12 may be one which prevents the exposure of the fluid medication 28 to ultraviolet radiation, one which is of low permeability to prevent the exposure of the fluid medication 28 to air, or one which is inert to prevent any derogatory interaction with the fluid medication 28. Material candidates for the body 12 include polycarbonate, polyester, nylon, glass filled plastic, and cyclic olefin copolymers. As seen in FIGS. 5 and 6, in the event such selected material is of relatively low strength as could increase its susceptibility to bursting upon the fracture of the quill 58 and release of the compressed gas into the piston chamber 20, the syringe 10 may be provided with an external, tubular reinforcement sleeve 74 which is advanceable over the outer surface of the barrel portion 24 of the body 12. As is best seen in FIG. 6, the reinforcement sleeve 74 is preferably cylindrically configured and formed such that when advanced over the barrel portion 24, it does not interfere with the engagement of the discharge orifice 30 to the injection site on the user's skin. As seen in FIG. 8, it is contemplated that the reinforcement sleeve 74 may be fabricated from a material which effectively magnifies the measurement indicia 49 when the reinforcement sleeve 74 is advanced over the barrel portion 24 of the body 12.

Additional modifications and improvements of the present invention may also be apparent to those of ordinary skill in the art. For example, the syringe 10 may be configured such that compressed gas is stored directly within the storage chamber 16, with an alternative fracturable release mechanism or member being disposed within the body 12 between the storage and piston chambers 16, 20. Additionally, the compressed gas cartridge 54 may be substituted with a spring which is released by the actuation of the trigger mechanism 62 and, upon such release, acts against the end face 23 of the piston 22 in a manner facilitating the advancement thereof into the delivery chamber 26 of the body 12. As such, the parts described and illustrated herein are intended to represent only certain embodiments of the present invention, and are not intended to serve as limitations of alternative devices within the spirit and scope of the invention.

What is claimed is:

1. A single use needleless syringe for administering a fluid medication, the syringe comprising:
   a hollow, tubular body comprising:
      a gas storage portion defining a storage chamber containing a quantity of a compressed gas;
      an ejector portion defining a piston chamber which is selectively placeable into fluid communication with the storage chamber and has a piston movably disposed therein;
      a barrel portion defining a delivery chamber for receiving a prescribed dosage of the fluid medication, the delivery chamber being oriented relative to the piston chamber such that the piston is advanceable into the delivery chamber; and
      a discharge orifice in fluid communication with the delivery chamber for allowing the fluid medication to be filled thereinto and expelled therefrom;
   a fracturable release member disposed within the body for preventing the flow of the compressed gas from the storage chamber into the piston chamber; and
   a trigger mechanism removably attachable to the body and comprising:
      a stem portion partially insertable into the body and engagable to the release member; and
      a head portion attached to the stem portion;
      wherein the application of compressive pressure to the head portion subsequent to the insertion of the stem portion into the body facilitates the fracture of the release member and resultant flow of the compressed gas into the piston chamber, the compressed gas acting against the piston in a manner forcing the piston into the delivery chamber which causes the fluid medication to be expelled therefrom via the discharge orifice.

2. The syringe of claim 1 further comprising a plunger member disposed within the delivery chamber for preventing the fluid medication filled into the delivery chamber from flowing into the piston chamber.

3. The syringe of claim 1 further comprising a safety member slidably attached to the body and selectively moveable between a locked position whereat the stem portion of the trigger mechanism is prevented from engaging the release member, and an unlocked position whereat the application of compressive pressure to the head portion of the trigger mechanism facilitates the fracture of the release member by the force of the stem portion acting thereagainst.

4. The syringe of claim 1 wherein:
   the gas storage, ejector and barrel portions of the body each have a generally circular cross-sectional configuration; and
   the storage, piston and delivery chambers are disposed in coaxial alignment with each other.

5. The syringe of claim 4 wherein the body is formed such that the diameter of the gas storage portion exceeds the diameter of the ejector portion, and the diameter of the ejector portion exceeds the diameter of the barrel portion.

6. The syringe of claim 4 further comprising a compressed gas cartridge which contains the compressed gas and is disposed within the gas storage portion, the compressed gas cartridge including the release member integrally formed thereon.

7. The syringe of claim 6 wherein:

the release member of the compressed gas cartridge comprises an elongate quill which extends axially into the piston chamber; and the stem portion of the trigger mechanism is radially insertable into the ejector portion of the body so as to extend in generally perpendicular relation to the quill;

wherein the application of compressive pressure to the head portion of the trigger mechanism subsequent to the insertion of the stem portion into the ejector portion of the body causes the stem portion to act against the quill in a manner which fractures the quill and results in the flow of the compressed gas from the compressed gas cartridge into the piston chamber.

8. The syringe of claim 7 further comprising:

a safety member slidably attached to the ejector portion of the body and having a slot formed therein;

the safety member being selectively movable between a locked position whereat the stem portion is received into the slot and prevented from radial movement by the engagement of the head portion to the safety member, and an unlocked position whereat the application of compressive pressure to the head portion facilitates radial movement of the stem portion toward the quill and the fracture thereof by the force of the stem portion acting thereagainst.

9. The syringe of claim 1 wherein:

the body includes an outer surface and an inner surface having a proximal section which defines the storage chamber, an intermediate section which defines the piston chamber, and a distal section which defines the delivery chamber; and the syringe further comprises a reactive coating which is applied to the intermediate section of the inner surface and adapted to change color when exposed to the compressed gas flowing from the storage chamber into the piston chamber upon the fracture of the release member by the trigger mechanism.

10. The syringe of claim 9 wherein the body is fabricated from a transparent material.

11. The syringe of claim 1 wherein:

the body includes an outer surface and an inner surface having a proximal section which defines the storage chamber, an intermediate section which defines the piston chamber, and a distal section which defines the delivery chamber; and the syringe further comprises a liner which is disposed within the storage chamber and extends along the proximal section of the inner surface for preventing leakage of the compressed gas from with the storage chamber.

12. The syringe of claim 1 wherein:

the body includes an outer surface and an inner surface having a proximal section which defines the storage chamber, an intermediate section which defines the piston chamber, and a distal section which defines the delivery chamber; and the syringe further comprises a liner which is disposed within the delivery chamber and extends along the distal section of the inner surface for maintaining the bioavailability of the fluid medication filled into the delivery chamber.

13. The syringe of claim 1 further comprising a tubular reinforcement sleeve advanceable over the barrel portion of the body.

14. The syringe of claim 13 wherein:

the barrel portion of the body includes measurement indicia disposed thereon; and the sleeve is fabricated from a material adapted to magnify the measurement indicia when advanced over the barrel portion.

15. The syringe of claim 1 wherein:

the compressed gas is liquified and contained within a compressed gas cartridge disposed within the gas storage portion; and the compressed gas cartridge is fabricated from a semi-transparent material to facilitate the visual observation of the liquified compressed gas therein.

16. The syringe of claim 15 wherein the body is fabricated from a transparent material.

17. A method for administering a fluid medication, comprising the steps of:

(a) providing a single use needleless syringe which includes:

a body having a gas storage portion defining a storage chamber containing a quantity of compressed gas, an ejector portion defining a piston chamber which is selectively placeable into fluid communication with the storage chamber and has a piston removably disposed therein, and a barrel portion defining a delivery chamber for receiving a prescribed dosage of the fluid medication;

a fracturable release member disposed within the body for preventing the flow of the compressed gas from the storage chamber into the piston chamber; and a trigger mechanism removably attachable to the body and including a stem portion having a head portion attached thereto;

(b) partially inserting the stem portion of the trigger mechanism into the body; and (c) applying compressive pressure to the head portion to facilitate the fracture of the release member and resultant flow of the pressurized gas into the piston chamber.

18. The method of claim 17 wherein the syringe further comprises a safety member slidably attached to the body, and step (b) comprises the steps of:

(1) moving the safety member to a locked position whereat the stem portion is prevented from engaging the release member when compressive pressure is applied to the head portion; and (2) moving the safety member to an unlocked position whereat the application of compressive pressure to the head portion will facilitate the fracture of the release member by the force of the stem portion acting thereagainst.

19. A single use needleless syringe for administering a fluid medication, the syringe comprising:

a hollow, tubular body comprising:

a gas storage portion defining a storage chamber containing a quantity of a compressed gas;

an ejector portion defining a piston chamber which is selectively placeable into fluid communication with the storage chamber and has a piston movably disposed therein;

a barrel portion defining a delivery chamber having a prescribed dosage of the fluid medication pre-filled thereinto, the delivery chamber being oriented relative to the piston chamber such that the piston is advanceable into the delivery chamber; and a discharge orifice in fluid communication with the delivery chamber for allowing the fluid medication to be expelled therefrom;

a fracturable release member disposed within the body for preventing the flow of the compressed gas from the storage chamber into the piston chamber;

wherein the fracture of the release member results in the flow of the compressed gas into the piston chamber, the compressed gas acting against the piston in a manner forcing the piston into the delivery chamber which causes the fluid medication to be expelled therefrom via the discharge orifice.

20. The syringe of claim 19 further comprising a trigger mechanism removably attachable to the body and comprising:

a stem portion partially insertable into the body and engagable to the release member; and a head portion attached to stem portion;

wherein the application of compressive pressure to the head portion subsequent to the insertion of the stem portion into the body facilitates the fracture of the release member.

21. The syringe of claim 19 further comprising a plunger member disposed within the delivery chamber for preventing the fluid medication pre-filled into the delivery chamber from flowing into the piston chamber.

22. The syringe of claim 19 further comprising a tubular reinforcement sleeve advanceable over the barrel portion of the body.

23. The syringe of claim 22 wherein:

the barrel portion of the body includes measurement indicia disposed thereon; and the sleeve is fabricated from a material adapted to magnify the measurement indicia when advanced over the barrel portion.

24. The syringe of claim 19 wherein:

the compressed gas is liquified and contained within a compressed gas cartridge disposed within the gas storage portion; and the compressed gas cartridge is fabricated from a semi-transparent material to facilitate the visual observation of the liquified compressed gas therein.

25. The syringe of claim 24 wherein the body is fabricated from a transparent material.

26. A single use needleless syringe for administering a fluid medication, the syringe comprising:

a hollow, tubular body comprising:

a gas storage portion defining a storage chamber containing a quantity of a compressed gas;

an ejector portion defining a piston chamber which is selectively placeable into fluid communication with the storage chamber and has a piston movably disposed therein;

a barrel portion defining a delivery chamber for receiving a prescribed dosage of the fluid medication, the delivery chamber being oriented relative to the piston chamber such that the piston is advanceable into the delivery chamber; and a discharge orifice in fluid communication with the delivery chamber for allowing the fluid medication to be filled thereinto and expelled therefrom;

a fracturable release member disposed within the body for preventing the flow of the compressed gas from the storage chamber into the piston; and a reactive coating applied to a selected portion of the body and adapted to change color when exposed to the compressed gas;

wherein the fracture of the release member facilitates the exposure of the reactive coating to the compressed gas and the resultant change in the color thereof.

27. The syringe of claim 26 wherein:

the body includes an outer surface and an inner surface having a proximal section which defines the storage chamber, an intermediate section which defines the piston chamber, and a distal section which defines the delivery chamber; and the reactive coating is applied to the intermediate section of the inner surface.

28. The needleless syringe of claim 1 wherein the body is fabricated from a material selected from the group consisting of:

polycarbonate;

polyester;

nylon;

glass filled plastic; and cyclic olefin copolymers.

29. The needleless syringe of claim 19 wherein the body is fabricated from a material selected from the group consisting of:

polycarbonate;

polyester;

nylon;

glass filled plastic; and cyclic olefin copolymers.

* * * * *